US008084440B2

(12) United States Patent
Van Den Elshout et al.

(10) Patent No.: US 8,084,440 B2
(45) Date of Patent: Dec. 27, 2011

(54) METHOD FOR IMPROVING THE FERTILITY OF ANIMALS

(75) Inventors: Wilhelmus Hubertus Henricus Antonius Van Den Elshout, Geleen (NL); Rudi Ludovicus Florent Forier, Zonhoven (BE)

(73) Assignee: Desol B.V., Susteren (NL)

( * ) Notice: Subject to any disclaimer, the term of this patent is extended or adjusted under 35 U.S.C. 154(b) by 603 days.

(21) Appl. No.: 11/918,749

(22) PCT Filed: Apr. 19, 2006

(86) PCT No.: PCT/EP2006/061673
§ 371 (c)(1),
(2), (4) Date: Dec. 13, 2007

(87) PCT Pub. No.: WO2006/111546
PCT Pub. Date: Oct. 26, 2006

(65) Prior Publication Data
US 2008/0139504 A1    Jun. 12, 2008

(30) Foreign Application Priority Data

Apr. 21, 2005 (EP) .................................. 05075950

(51) Int. Cl.
*A61K 31/715* (2006.01)
*A61K 31/497* (2006.01)
(52) U.S. Cl. ..................................... 514/54; 514/254.09
(58) Field of Classification Search ................... 514/54, 514/254.09
See application file for complete search history.

(56) References Cited

U.S. PATENT DOCUMENTS

| 2,925,341 | A | 2/1960 | Kaemmerer |
| 2,943,938 | A | 7/1960 | De Zeeuw et al. |
| 5,702,719 | A | 12/1997 | Donzis |
| 6,174,541 | B1 | 1/2001 | Song et al. |
| 6,306,453 | B1 | 10/2001 | Kurzinger |
| 2004/0097584 | A1 | 5/2004 | Graus et al. |

FOREIGN PATENT DOCUMENTS

| JP | 60-161920 | 8/1985 |
| JP | 2002-281914 | 10/2002 |
| RU | 2 063 749 | 7/1996 |
| WO | WO 01/64205 A2 | 9/2001 |
| WO | WO 02/37988 A1 | 5/2002 |
| WO | WO 02/091850 A1 | 11/2002 |
| WO | WO 2004/014320 A2 | 2/2004 |
| WO | WO 2004/066863 A2 | 8/2004 |
| WO | WO 2004/105775 A1 | 12/2004 |
| WO | WO 2005/034942 A1 | 4/2005 |

OTHER PUBLICATIONS

Svihus et al, "Changes in extract viscosity, amino acid content, and soluble and insoluble β-glucan and dietary fibre content of barley during different high moisture storage conditions", Animal Feed Science Technology, vol. 64, 1997, pp. 257-272.
Davis et al, "Aloe vera and Gibberellin—Anti-inflammatory Activity in Diabetes", Journal of The American Podiatric Medical Association, vol. 79, No. 1, Jan. 1989, pp. 24-26.
Database WPI Week 199407, XP002395145 & CN 1 071 200 A, Apr. 21, 1993.
Kim et al, "Estimation of soluble β-glucan content of yeast cell wall by the sensitivity to Glucanex® 200G treatment", Enzyme and Microbial Technology, vol. 35, 2004, pp. 672-677.
International Search Report mailed Sep. 9, 2006 in PCT/EP2006/061667.
International Search Report mailed Aug. 28, 2006 in PCT/EP2006/061658.
U.S. Appl. No. 11/918,721 (Elshout, Van Den et al.) filed Oct. 18, 2007 (International Application Filing Date Apr. 19, 2006).
U.S. Appl. No. 11/918,755 (Elshout, Van Den et al.) filed Oct. 18, 2007 (International Application Filing Date Apr. 19, 2006).
Toniolli et al, "Effect of Indole-3-Acetc Acid (Plant Auxin) on Boar Sperm Motility and Pregnancy and Prolificacy Rates After Freezing and Thawing", Reproduction In Domestic Animals, vol. 33, 1998, pp. 33-38.
Bumford, "Food and Reproduction of Wild House Mice III. Experiments on the Breeding Performance of Caged House Mice Fed Rice-Based Diets", Australian Wildlife Research, vol. 14, 1987, pp. 207-218.
El Mofty, "Induction of Sexual Reproduction in *Opaline sudafricana* by Injecting Its Host *Bufo regularis* with Gibberellic Acid", International Journal of Parasitology, vol. 4, 1974, pp. 203-206.
Xiao et al, "β-Glucan enhancement of T cell IFNγ response in swine", Veterinary Immunology and Immunopathology, vol. 102, 204, pp. 315-320.
Olsen, "The Stimulating Effect of a Phytohormone, Gibbberellic Acid, on Reproduction of *Mus musculus*", Australian Wildlife Research, vol. 8, 1981, pp. 321-325.
The Atlantic Swine Research Partnership Inc. Annual Report, Year Ended Dec. 31, 2004, pp. 1-34.
International Search Report mailed Jul. 18, 2006 in PCT/EP2006/061673.

*Primary Examiner* — Shaojia Anna Jiang
*Assistant Examiner* — Everett White
(74) *Attorney, Agent, or Firm* — Nixon & Vanderhye P.C.

(57) ABSTRACT

This invention is in the field of animal food, in particular food for female animals in their reproductive phase. Food according to the invention improves the fertility of animals and increases their chances on a pregnancy. It was found that the fertility of animals may be improved by feeding the animal with a certain amount of naturally occurring immune enhancing ingredients such as beta-glucans and/or phytohormones like auxin or gibberellic acid. Also, combinations of these substances, in particular the combination of beta-glucans and phytohormones, were shown to have a synergistic effect in that they improved the fertility of the animal more than these individual components on their own.

7 Claims, No Drawings

METHOD FOR IMPROVING THE FERTILITY OF ANIMALS

This application is the US national phase of international application PCT/EP2006/061673 filed 19 Apr. 2006 which designated the U.S. and claims benefit of EP 05075950.5, dated 21 Apr. 2005, the entire content of which is hereby incorporated by reference.

This invention is in the field of animal food, in particular food for female animals in their reproductive phase. Food according to the invention improves the fertility of animals and increases their chances on a pregnancy.

A wealth of literature has been published on the treatment of infertility in man and animals. Reproductive medicine has revealed a great number of treatments that have good success rates for many different indications.

Clomiphene citrate is a commonly prescribed fertility drug. It stimulates the brain to release luteinizing hormone, which causes egg maturation and release from the ovary. The drug is taken for just a few days and then stopped. A brief fertile period may follow. A drawback is that more than one egg may be released, resulting in a multiple pregnancy. In addition, nearly half of all pregnancies achieved in this way result in spontaneous abortion. Perhaps the miscarriage rate is so high because such medications only force ovulation without correcting underlying deficiencies or hormonal abnormalities.

Botanical medicines on the other hand, nourish and support the female reproductive system to restore hormonal balance. Many dietary supplements have been described that function in improving the fertility of man and animals.

In order to improve reproductive health of male and female animals it has been recommended to feed a good multivitamin preparation and include sufficient amounts of supplements in the diet, such as zinc, vitamin E and the amino acids arginine and taurine.

Because semen contains high concentrations of zinc, supplementing the diet with 30-60 mg zinc a day may improve sperm count and sexual function. A good dietary source of zinc is pumpkin seeds, long recommended as a fertility-enhancing food and a remedy for benign prostate enlargement. Pumpkin seeds also are rich in two other nutrients beneficial to male sexual functioning: the plant steroid beta-sitosterol (which binds to the testosterone receptor) and vitamin E.

Vitamin E has previously been labeled the anti-sterility vitamin. Vitamin E is crucial to proper reproductive function in both men and women. In fact, the chemical name for vitamin E, "tocopherol," originated from the Greek words tokos, which means "offspring," and phero, which means "to bear." One of the body's main antioxidant nutrients, vitamin E protects hormones from oxidation. As vitamin E becomes less available in processed foods and exposure to harmful oxidizing agents increases, supplementation with 400-800 IU a day may improve fertility for some men.

Arginine has been shown to raise sperm counts and sperm motility. The recommended dosage is 2-4 g a day. Taurine, another amino acid that may enhance sperm production and motility, is supplemented at 2-4 a day.

The following herbs are often recommended by naturopathic doctors and herbalists to help restore female fertility.

Chaste tree berry (Vitex agnus-castus): This herb stimulates the release of luteinizing hormone (LH) from the pituitary gland in the brain. This, in turn, promotes ovulation. Chaste tree berry may restore normal periods in women with amenorrhea (lack of menstrual periods).

Dong quai (Angelica sinensis): Widely used for female complaints, including menstrual irregularities and infertility, dong quai can tone a weak uterus by promoting metabolism within the organ, 12 regulating hormonal control and improving the rhythm of the menstrual cycle.

Red clover blossoms (Trifolium pratense): These beautiful little flowers are categorized in many herbals as fertility promoters. Chemical analysis shows that the herb is rich in coumestans and isoflavones, estrogenlike compounds that may promote fertility, particularly in women who are deficient in estrogen.

Licorice (Glycyrrhiza glabra): This plant contains hormonally active compounds categorized as saponins. A Japanese study found licorice-based medicines improved menstruation in women with infrequent periods. The study also found that licorice helped women with elevated testosterone and low estrogen levels, as commonly occurs in polycystic ovary disease.

Siberian ginseng (Eleutherococcus senticosus): This and other tonic botanicals can improve fertility by enhancing overall health and vitality. Siberian ginseng also acts on the brain to promote regulation of reproductive hormones.

Despite all these products that may improve the fertility of animals, there is still room for alternative products that can play a role in this process.

Surprisingly, it has now been found that the fertility of animals may be improved by feeding the animal with a certain amount of naturally occurring immune enhancing ingredients such as beta-glucans and/or phytohormones like auxin or gibberellic acid. Also, combinations of these substances, in particular the combination of beta-glucans and phytohormones, were shown to have a synergistic effect in that they improved the fertility of the animal, even more than these individual components on their own.

The invention therefore relates to the use of an animal feed comprising between 0.05 and 500 milligram of beta-glucans per kilogram of feed and/or between 0.1 and 1000 milligram of phytohormones per kilogram of feed for improving the fertility of animals.

The term infertile animals or animals with impaired fertility is used herein to refer to animal populations that have difficulties in getting pregnant. In particular however, the term is used to indicate individual animals that have difficulties in getting pregnant. The invention proved particularly useful for getting animals into heat earlier, so that they produced offspring earlier resulting in an increased number of offspring of the total population. It was also observed that the number of newborns per parent animal increased by using the method according to the invention. This is particularly useful in commercial stock farming where even small increases in the productivity of the stock may contribute significantly to the commercial profits.

Improving the fertility of animals as used herein also relates to increasing the number and/or quality of the offspring of animals, in particular vertebrate animals, more in particular domestic animals such as farm animals. Farm animals are animals that are kept for profit, such as for instance animals selected from the group consisting of cattle such as cows, pigs, horses, rabbits, deer, ostrich or fur-animals like mink. The term animals as used herein is particularly intended to exclude humans.

The causes of reduced fertility or even infertility are not yet completely understood. Even in animal populations that are completely germ-free such phenomena exist. The effects in this study were observed in an otherwise healthy population.

Mortality rates in the control group were the same as the mortality rates in the group that received the feed according to the invention.

Phytohormones are herein defined as molecules that function to coordinate plant growth and development. The compounds that have been considered as plant hormones are for instance: indole-3-acetic acid (auxin), cytokinin, gibberellin, ethylene, abscisic acid. In addition, brassinosteroids, jasmonic acid and salicylic acid have been shown to have important growth regulating activities and are considered to function as phytohormones.

The invention therefore particularly relates to a method wherein the phytohormone is selected from the group consisting of indole-3-acetic acid (IAA, auxin), cytokinin, gibberellin, gibberellic acid, ethylene, abscisic acid, brassinosteroids, jasmonic acid and salicylic acid.

Particularly good results were obtained when the animal feed was supplemented with free IAA instead of conjugated IAA. Free IAA and conjugated IAA are known compounds. Free IAA is a naturally-occurring plant growth phytohormone which has been extensively studied. In plants, most of the IAA occurs in a conjugated form (Slovin et al. 1999, Biochemistry and molecular biology of plant hormones, Elsevier, Amsterdam. P115-140), either conjugated to sugars via ester linkages or to amino acids and peptides via amide linkages.

Free IAA is readily available as a commercial product. It may be synthesised chemically or prepared in a biological way. IAA producing micro-organisms are widespread in nature. Yeast, fungi and many bacteria as well as plants are known to convert precursors of IAA into free IAA. In addition to the L-tryptophan conversion by bacteria, also L-tryptophan independent biochemical routes towards free IAA are described extensively (J. Plant Growth Regul (2001) 20: 198-216).

A well known bacterium, capable of producing free IAA is Azospirillum Brasilense (AB). At the end of the growth phase in a regular fermentation process, AB is able to convert L-tryptophan into free IAA. To increase the efficiency of this conversion, a small amount of synthetic free IAA may be added to the media. Via a feedback mechanism, AB increases the conversion of L-tryptophan into free IAA.

Final concentrations of 1 gram free IAA/liter culture broth are easy to make, but even much higher concentrations are possible, depending on the micro-organism used.

After ending the fermentation, the micro-organism may be lysed and a powder enriched in free IAA may be obtained by spray drying or any other convenient way of drying the culture broth. Other techniques may be used to remove liquids partly or completely.

The term "free IAA" is used herein to indicate that the free IAA is in the free or acid form, whereas the term "conjugated IAA" refers to IAA that is conjugated via ester linkages or via amide linkages.

As long ago as 1956, the effects of free IAA on humans were studied, and it was shown that single doses of 0.1 g/kg body weight were non-toxic (Mirsky A and Diengott D, Hypoglycemic action of indole-3-acetic acid by mouth in patients with diabetes mellitus, Proc. Soc. Exp. Biol. Med. 93: 109-110.1956). In 1964, it was found that photo-oxidation products of free IAA acted as growth inhibitors of micro-organisms (Still C, Fukuyama T and Moyed H, Inhibitory Oxidation Products of Indole-3-acetic acid, J. Biological Chemistry, 240.6, 2612-2618, 1964).

Also, the medical use of free IAA and some of its derivatives has previously been described. EP 1.296.676 describes the use of free IAA as a pharmaceutical, in particular for treating neoplastic disease in humans. WO 02/080906 describes the use of free IAA for treating endometriosis in women. Nachson et al. (Feed and Chemical Toxocology 41, 745-752) reported the effect of some free IAA derivates (indole-3-carbinol and 3,3'-diindolylmethane) on the proliferation and induction of apoptosis in human prostate cancer cell lines whereas Rossiter et al. (Bioorganic & Medicinal Chemistry Letters, 12, 2523-2526) as well as Folkes et al. (Biochemical Pharmacology 63, 265-272) described the use of free IAA and some derivatives in enzyme-pro-drug directed cancer therapies.

Animal feed comprising IAA has been described in the art, for instance, U.S. Pat. No. 2,925,341 discloses a feed additive which comprises 10-50 mg of indole acetic acid per kilogram of feed.

It was found in our studies that phytohormones and beta-glucans appeared to work in a wide range of concentrations for improving the fertility of animals. The optimal concentrations may vary between different species, however, the skilled person will know how to obtain an optimal concentration for a given species, for instance by titration of the desired compound into the animal feed and testing when this would have the optimal effect. The following may serve as guidance in this process.

A skilled person will appreciate that the amount of free IAA in the ready to use feed has to be adjusted in order to supply the animal with an effective amount of free IAA. In order to adjust the free IAA concentration in the feed so that a certain daily intake of free IAA is achieved, an estimate has to be made of the feed intake of an animal or animal group. A skilled person is aware of the feed intake of a particular (kind or group of) animal(s). Typically, the feed intake per day is between 0.5 and 10% of the body weight of the animal, with occasional exceptions as high as 20%. Elderly animals tend to eat less and are considered to have a feed intake per day between 0.1 and 5%, typically of 1% of their body mass.

It was found that fertility of animals was improved when free IAA was provided in their feed in the range of 0.004 and 40 mg per kilogram life weight per day (mg/kglw/day). Optimum between cost and benefit was reached in concentrations between 0.04 and 4 mg/kglw/day, in particular feeding with 0.4 mg/kglw/day free IAA was very effective.

The invention therefore also relates to a process for improving the fertility of an animal wherein the animal is fed with free IAA provided in the feed in the range of 0.004 and 40 mg per kilogram life weight per day (mg/kglw/day).

It was also found that, within the family of beta-glucans, in particular 1,3 and 1,6 beta glucans were very useful to improve the fertility of animals. A particularly good source of such 1,3 and 1,6 beta glucans may be found in preparations of *Agaricus blazei* murill (ABM) or yeast cell walls. Animal feed supplemented with 1 to 1000 mg/kglw/day of dried *Agaricus blazei* murill was found to produce the desired effect of improving the fertility of animals. This corresponds to approximately 0.1 to 100 mg/kglw/day of 1,3 and 1,6 beta glucans. Excellent results were obtained when the animals were fed with 1 to 10 mg/kglw/day of 1,3 and 1,6 beta glucans, optimum of cost benefit was found to be around 5 mg/kglw/day, corresponding to 50 mg/kglw/day of dried ABM.

The invention therefore also relates to a process for improving the fertility of an animal wherein the animal is fed with 1,3 and 1,6 beta glucans in the range of approximately 0.1 to 100 mg/kglw/day.

Animal feed comprising beta-glucans is readily available. For instance, WO 02/091850 A discloses an animal feed which comprises. 100-1000 mg of beta-glucans per kilogram of feed. Also, WO 02/37988, WO 2004/066863, WO 2004/014320 and US 2005/020490 A1 disclose compositions which comprise beta-glucans, and which may be suitable for use as an animal feed in the present invention. Such animal feed has also been described in Hiss and Sauerwein, Journal of animal physiology and animal nutrition, 87, 2003, pp 2-11, Deblackwell, Berlin.

The effect of improving the fertility of animals was also observed when the feed of animals was supplemented with Gibberelin or Gibberellic acid. The optimal concentrations here were found to be within the range of 0.0004 and 4 mg/kglw/day. The effect of improving the fertility of animals was particularly pronounced in the range of 0.004 and 0.4 mg/kglw/day. Optimal results were achieved between 0.01 and 0.1 mg/kglw/day, such as 0.04 mg/kglw/day.

Suitable feed substances that may be used in the present invention have been described. U.S. Pat. No. 2,943,938 and Svihus et al. (Journal of Animal Science, 64, 1997, p 257-272) describe an animal feed which may comprise suitable amounts of giberellic acid per kilogram of composition.

As a consequence, the invention is therefore also directed towards the use of any of the substances described above, for the preparation of a medicament for improving the fertility of animals.

EXAMPLES

Example 1

Microbiological Production of a Preparation Containing Free IAA

*Azospirillum brasilence* Sp7 (ATCC) was obtained as an agar culture in a culture tube. LB medium was used to grow the strain overnight at 28° C. at 175 rpm. Glycerol was added to the culture up to 10%, mixed and divided over Nalgene creovials and frozen at −80° C. Stocks were stored at −80° C. in creovials.

To prepare a seed culture of *A. brasilence*, one stock (1.2 to 1.8 ml) was thawed and added to 1 liter of LB medium and grown for about 20 h at 28° C. and 175 rpm to an Optical Density (OD620 nm) of about 2.5.

A 10 liter fermentor was rinsed with water and the pH electrode was calibrated. Nine liter of LB medium was prepared and 1 g/l L-Tryptophan and 0.1 g/l free IAA was added. The medium was entered into the fermentor together with 2 ml of anti foam. The fermentor was sterilised for 30 min at 121° C. After cooling down to 28° C., the O2 probe is calibrated with N2 and O2, 0 and 100% air saturation respectively.

The seed culture is transferred to the fermentor via a flask and tubing which are separately sterilised in an autoclave. When the addition is completed the tubing and flask are removed and the fermentation is started with the following parameters:

| | |
|---|---|
| Stirrer speed | 400 rpm |
| Temperature | 28° C. |
| Aeration | 0.75 Nl/min |
| PH | 7 |

After 15 min a sample is taken to measure the OD620 nm and check the pH. Samples are taken at certain intervals to quantify the growth of *A. brasilence*. When the growth rate declined extra medium was added to ensure that enough biomass was formed for the production of free IAA. It was found that the production of free IAA started when the active growth phase ended and continued for a prolonged period. The course of the free IAA concentration was followed by LC-MS. When the concentration of free IAA was at a level of about 1 g/l, the fermentation was terminated and the cells were harvested and lysed by means of a nonojet homogeniser at about 1400 bar. The remaining supernatant and the lysed cells were sterilised and spray dried to yield the desired product formulation.

Example 2

Preparation of Pig Feed Containing Beta Glucans

An amount of 50 gram of dried *Agaricus Blazei* Murill (*Agaricus* Farm), a natural source of beta-glucans was suspended in 100 ml of olive oil. A pig feed according to the invention was prepared by vacuum impregnating ten kilogram of the usual commercially available pig feed with 100 ml of the oil suspension. Control feed was prepared by vacuum impregnating the same amount of feed with only olive oil.

Example 3

Preparation of Pig Feed Containing Plant Growth Hormones

An amount of the spray dried formulation as described in example 1 corresponding to 400 milligram of free IAA was suspended in 100 ml of olive oil. A pig feed according to the invention was prepared by vacuum impregnating ten kilogram of the usual commercially available pig feed with 100 ml of the oil suspension. Control feed was prepared by vacuum impregnating the same amount of feed with only olive oil.

Example 4

Preparation of Pig Feed Containing Both Beta Glucans and Plant Growth Hormones

An amount of 50 gram of dried *Agaricus Blazei* Murill (*Agaricus* Farm), a natural source of beta-glucans and an amount of the spray dried formulation as described in example 1 corresponding to 400 milligram of free IAA were suspended in 100 ml of olive oil. A pig feed according to the invention was prepared by vacuum impregnating ten kilogram of the usual commercially available pig feed with 100 ml of the oil suspension. Control feed was prepared by vacuum impregnating the same amount of feed with only olive oil.

Example 5

Improving the Fertility of Sows

Objective of the study was to determine whether a diet supplemented with free IM and/or beta-glucans could improve the fertility of sows.

The weaning period of porcine species constitutes a particularly delicate moment from the physiological, metabolic and endocrine point of view. Numerous studies reported that few days before the weaning as well as few days after that, a greater energetic and amino acid food contribution is fundamental in order to adequately stimulate follicular and ovulatory dynamics and therefore to obtain a better reproductive efficiency with favourable implications, mainly on management.

Several sows do not respond to this type of nutritional treatment (higher energy plus amino acid complement). The reproductive efficiency lowers during summer-autumn period; this feature is described as negative seasonal effect.

In order to regulate follicular dynamics and ovulation rate, one of the most frequent protocols is the hormonal treatment by using exogenous gonadotropins. The hormonal treatments with exogenous substances are currently prohibited by most health guidelines and from a perspective of animal well-being. This holds in particular for the production lines of biological pig.

The experiment was performed in three well-managed animal farms specialised in pork production for the traditional pork butchery (ham, for example). Forty lactating sows were randomly distributed into four groups of 10 sows, three groups were fed with feed according to the invention, one group received control feed. The animals received the feed the 3 last days of lactation until 3 days after weaning.

Inclusion criteria for the study were:
Sows that delivered from at least 21 days
Sows not submitted to veterinary treatments
Sows without post-partum anorexia
Sows with prolificacy of 10 or more at the last delivery
Sows that nurses at least 9 piglets
The BCS is not comprised in the inclusion criteria; backfat will not be considered.

Exclusion criteria were:
Sows that the breeding technician will eliminate after the weaning
Sows subordinates to veterinary treatments
Sows with viral infections, in particular PRSV
Sows with syndrome mastitis-metrite-agalaxia
Sows with limb lesions
Sows with fever and anorexia during lactation The administration of the feed supplement was performed in the morning in concentrations indicated in table 1. After weaning, the pigs were placed in "fecundation" cages and stimulated two times per day with boars skilled for oestrous detection. Oestrous sows were then inseminated by a technician following the classical protocol.

Sows were diagnosed for pregnancy in the $3^{rd}$ or $4^{th}$ week after insemination using ultrasonography. The prolificacy of each sow was registered after parturition.

From the first results of the experiment it was observed that sows treated with the feed according to the invention had a better metabolic and endocrine status and presented an optimal weaning/oestrus period (5 days) as well as a better follicular dynamics which all translated into a higher percentage of pregnant sows and a higher number of offspring.

TABLE 1

| | feed additives for pig feed |
|---|---|
| Group 1 | 0.4 mg/kglw/day free IAA |
| Group 2 | 50 mg/kglw/day of dried ABM corresponding to 5 mg/kglw/day of 1.3-1.6 beta glucan |
| Group 3 | 0.4 mg/kglw/day free IAA plus 50 mg/kglw/day of dried ABM corresponding to 5 mg/kglw/day of 1.3-1.6 beta glucan |
| Group 4 (control) | none |

The invention claimed is:

1. A method for improving fertility of a vertebrate female animal comprising administering an animal feed comprising between 1 and 100 milligrams of indole-3-acetic acid per kilogram of feed to a vertebrate female animal in need of improved fertility in an amount to achieve between 0.004 and 40 milligram of the indole-3-acetic acid per kilogram life weight of the vertebrate female animal per day sufficient to improve the fertility of the animal.

2. Method according to claim 1, wherein the indole-3-acetic acid consists of free indole acetic acid (IAA).

3. Method according to claim 1, wherein the composition additionally comprises beta glucans.

4. Method according to claim 3 wherein the beta glucans are administered in a concentration between 0.1 and 100 milligrams per kilogram life weight of the vertebrate animal per day.

5. Method according to claim 4 wherein the beta glucans are administered in a concentration between 1 and 10 milligrams per kilogram life weight of the vertebrate animal per day.

6. Method according to claim 4 or 5, wherein the beta-glucans comprise 1,3 and/or 1,6 glucans.

7. Method according to claim 1, wherein the animal feed administered to the vertebrate female animal comprises between 10 and 100 milligrams of indole-3-acetic acid per kilogram of feed.

* * * * *